United States Patent [19]
Pelton et al.

[11] Patent Number: 5,843,244
[45] Date of Patent: Dec. 1, 1998

[54] SHAPE MEMORY ALLOY TREATMENT

[75] Inventors: Alan Pelton; Thomas Duerig, both of Fremont, Calif.

[73] Assignee: Nitinol Devices and Components, Freemont, Calif.

[21] Appl. No.: 661,305

[22] Filed: Jun. 13, 1996

[51] Int. Cl.$^6$ .................................................... C22F 1/10
[52] U.S. Cl. ........................................... 148/563; 148/676
[58] Field of Search ................................. 148/402, 563, 148/676, 670

[56] References Cited

U.S. PATENT DOCUMENTS 4,502,896  3/1985  Duerig et al. ........................... 148/402

FOREIGN PATENT DOCUMENTS

| 201028/85 | 9/1985 | Japan . | |
|---|---|---|---|
| 62-60851 | 3/1987 | Japan | 148/563 |
| 62-284047 | 12/1987 | Japan | 148/563 |

Primary Examiner—George Wyszomierski
Attorney, Agent, or Firm—Dean Garner

[57] ABSTRACT

A method of treating a component formed from a Ni—Ti based shape memory alloy, so that the component exhibits superelasticity, comprises cold working the component, annealing the alloy while the component is restrained in the configuration resulting from the cold working step, and exposing the component to a temperature that is less than the solvus temperature of the alloy and greater than the temperature to which it is exposed in the annealing step to cause the $A_f$ temperature to be reduced.

8 Claims, 1 Drawing Sheet

SHAPE MEMORY ALLOY TREATMENT

BACKGROUND TO THE INVENTION

This invention relates to a method of treating a component formed from a shape memory alloy, in particular so that the component exhibits enhanced elastic properties.

Articles formed from shape memory alloys can exhibit shape memory properties associated with transformations between martensite and austenite phases of the alloys. These properties include thermally induced changes in configuration in which an article is first deformed from a heat-stable configuration to a heat-unstable configuration while the alloy is in its martensite phase. Subsequent exposure to increased temperature results in a change in configuration from the heat-unstable configuration towards the original heat-stable configuration as the alloy reverts from its martensite phase to its austenite phase.

Shape memory alloys can exhibit enhanced elastic properties compared with materials which do not exhibit martensite-austenite transformations and it is these properties that the present invention is concerned with in particular. The nature of the superelastic transformations of shape memory alloys is discussed in "Engineering Aspects of Shape Memory Alloys", T. W. Duerig et al, on page 370, Butterworth-Heinemann (1990). Subject matter disclosed in that document is incorporated in this specification by this reference to the document. A principal transformation of shape memory alloys involves an initial increase in strain, approximately linearly with stress. This behaviour is reversible, and corresponds to conventional elastic deformation. Subsequent increases in strain are accompanied by little or no increase in stress, over a limited range of strain to the end of the "loading plateau". The loading plateau stress is defined by the inflection point on the stress/strain graph. Subsequent increases in strain are accompanied by increases in stress. On unloading, there is a decline in stress with reducing strain to the start of the "unloading plateau" evidenced by the existence of an inflection point along which stress changes little with reducing strain. At the end of the unloading plateau, stress reduces with reducing strain. The unloading plateau stress is also defined by the inflection point on the stress/strain graph. Any residual strain after unloading to zero stress is the permanent set of the sample. Characteristics of this deformation, the loading plateau, the unloading plateau, the elastic modulus, the plateau length and the permanent set (defined with respect to a specific total deformation) are established, and are defined in, for example, "Engineering Aspects of Shape Memory Alloys", on page 376.

Shape memory alloys are also discussed in an article by L. McDonald Schetky in the Encyclopedia of Chemical Technology (edited by Kirk-Othmer), volume 20 pages 726 to 736. Subject matter disclosed in that document is incorporated in this specification by this reference to the document.

The transformation from austenite to martensite on cooling begins at a temperature known as the $M_s$ temperature, and is completed at a temperature known as the $M_f$ temperature. The transformation of martensite to austenite upon heating begins at a temperature known as the $A_s$ temperature and is complete at a temperature known as the $A_f$ temperature. The application of a load tends to favour, or stabilise the martensite phase. Non-linear superelastic properties are exhibited when the austenitic phase is stable in the absence of a load, yet the martensitic phase can temporarily become the stable phase when a load of sufficient magnitude is introduced. Thus these properties require that one maintains the material temperature slightly above the $A_f$ temperature. The temperature above which all traces of superelasticity are lost is called the $M_d$ temperature.

A preferred way in which non-linear superelastic properties can be introduced in a shape memory alloy involves cold working the alloy by one of several deformation methods, for example, swaging, drawing, pressing, stretching or bending. The cold working step is followed by an annealing step at a temperature less than the recrystallization temperature of the alloy, for a time sufficient to cause dislocations to rearrange, combine and align themselves (so-called "recovery" processes). The resulting recovered dislocation structure should ideally be dense enough to make plastic deformation difficult, but not so dense as to prevent the martensite phase from transforming upon the application of a load, and growing in a relatively unimpeded manner.

Since many preferred superelastic alloys are thermally unstable in the temperature range in which these recovery processes occur, a second unavoidable result of this recovery heat treatment step is to age the material, that is to cause Ni-rich particles to precipitate, having the effect of enriching the matrix phase in titanium, and thus increasing the transformation temperatures (including the $A_f$ temperature). Optimum superelastic properties are only realized when using shape memory alloys above the $A_f$ temperature, though it should be noted that some indications of superelasticity are observed above the $A_s$, temperature (typically 2° to 20° C. below $A_f$). Thus a second requirement for this recovery heat treatment is that $A_f$ not be increased above the temperature at which the alloy is to be used. Practically speaking this places upper limits on the time and temperature which can be used in the recovery heat treatment.

It is often the case that a device is to be used in a shape other than that which can be practically produced by cold working processes. For example, a straight wire can be conveniently produced by cold drawing, but a wire loop or other formed shape cannot be. In this case, it is customary to form the drawn, cold worked wire into the desired "heat stable" shape, to constrain the wire in that shape, and then to perform the above described recovery heat treatment to "shape set" the component. In this case the final annealing operation has two purposes: to adjust the superelastic properties of the alloy, and to properly set the shape of the article. The time and temperature of this heat treatment step are critical. If held too long at temperature, the material overages, causing the $A_f$ temperature to rise above the application temperature. If the annealing temperature is too short, or the temperature too low, the shape will be insufficiently formed, and too much of the original dislocation structure will remain to allow free martensite movement. This "forming" treatment may introduce still further cold work into the part, but that cold work is usually small compared to that introduced into the wire by drawing. Moreover, forming operations are often not uniform, and thus forming itself is not generally a convenient way to introduce cold work.

Articles of complicated shape require extensive forming and are very difficult to produce according to the above process. If the forming process causes strains which are too severe, the article will fracture as it is heated to the shape setting and recovery temperature (one is able to restrain the formed article, but cannot maintain its shape during the heating process without causing fracture). It is possible to overcome this problem by performing a series of smaller, intermediate shape setting operations which accumulate to provide the desired final shape, but unfortunately each of these shape setting operations requires sufficient annealing time to allow the material to soften, in preparation for the next. When accumulated, these heat treatments cause a cumulative ageing effect that can cause the $A_f$ temperature to rise beyond the expected service temperature (37° C. for most medical applications, for example).

It is also known that one can introduce superelasticity by solution treating and ageing, abandoning all attempts to retain cold work. Although this approach resolves the above problems, it leads to inferior superelastic properties, producing articles that are susceptible to fatigue and storage problems.

SUMMARY OF THE INVENTION

The present invention provides a technique for treating a component formed from a shape memory alloy so that the component exhibits enhanced elastic properties, which includes a step of briefly heating the component at an elevated temperature that is higher than the temperature of the shape setting treatment referred to above.

Accordingly, in one aspect, the invention provides a method of treating a component formed from a Ni—Ti based shape memory alloy so that the component exhibits superelasticity, which comprises:

(a) cold working the component, (b) heat treating the alloy while the component is restrained in a desired shape at a temperature that is less than the recrystallisation temperature of the alloy, to cause the dislocations in the alloy resulting from the cold working step to combine, and (c) exposing the component to a temperature that is greater than the temperature to which it is exposed in the shape setting step and less than the solvus temperature of the alloy, to cause the $A_f$ temperature to be reduced.

It has been found surprisingly that brief exposure of the component to elevated temperature after the cold working and shape setting steps can result in increases in the $A_f$ temperature of the alloy caused by the cold working and annealing steps to be reduced and often in a reduction in the $A_f$ temperature. This has the significant advantage of enabling the method of the invention to be used to make a component whose configuration is so complicated that it requires several cold working steps, while still making it possible to achieve shape memory properties (including enhanced elastic properties) with appropriate transformation temperatures. Surprisingly, this adjustment in the shape memory properties of the alloy can occur rapidly, and can be obtained without significant loss of the cold work previously imparted to the article. The treatment provided by the present invention makes it possible to shape set complex formed articles with less concern for overaging and degradation of superelastic properties.

Preferably, the amount of cold work imparted to the component after any full annealing treatment and prior to step (a) of the method is greater than about 10%, more preferably greater than about 20%. The technique for imparting the cold work will be selected according to the configuration of the article that is to be made and to the nature and configuration of the starting materials. Examples of suitable techniques include swaging, drawing, pressing and so on. Examples of configurations for the starting materials include sheet, bar, wire, rod, tube and so on.

The annealing temperature used in step (b) of the method will be selected so that configuration resulting from the cold working step is substantially retained after the means by which the component is restrained is released. Complex shapes may require one or more intermediate constrained heat treatments in order to achieve the final desired shape. Preferably the temperature to which the component is heated in these shape setting steps is kept as low as possible to minimise aging effects on the alloy, which can result in loss of strength or ductility or both. Preferably, the temperature to which the component is heated in the annealing step of the method is no higher than about 40° C. below the solvus temperature, more preferably no higher than about 80° below the solvus temperature, for example no higher than about 100° below the solvus temperature. The temperature to which the component is heated will preferably be no lower than about 300° below the solvus temperature, more preferably no lower than about 250° below the solvus temperature, for example no lower than about 100° below the solvus temperature. Preferably, the temperature to which the component is heated in these shape setting steps of the method are no higher than about 540° C. and preferably no higher than about 510° C. The temperature to which the component is heated will preferably be no lower than about 270° C., more preferably no lower than about 300° C. The duration of each constrained heat treatment should be no less than 1 minute.

The elevated temperature to which the component is heated in step (c) of the method is preferably at least about 10° C. higher than the shape setting temperature to which the component is heated in step (b), more preferably at least about 20° higher. Preferably, the temperature to which the component is heated in step (c) of the method is no lower than about 70° C. below the solvus temperature, more preferably no lower than about 50° below the solvus temperature, for example no lower than about 30° below the solvus temperature. The treatment will generally be performed at a temperature of at least 480° C. The temperature will be below the solvus temperature of the alloy. The solvus temperature is the temperature below which a Ni-rich precipitate forms when the alloy is subjected to an aging heat treatment.

Preferably, the article is exposed to the elevated temperature in step (c) of the method for not more than about 10 minutes, more preferably not more than about 3 minutes. Preferably, it is exposed to the temperature for at least about 10 seconds, more preferably at least about 1 minute. Although cooling rates after this treatment are not considered critical, it is preferable to avoid cooling rates so slow as to allow re-precipitation of nickel-rich particles.

Preferably, step (c) of the method is carried out while the component is constrained in a desired shape, which will frequently be the same as the shape in which it is constrained during step (b). If step (c) is carried out while the component is not so constrained, the exposure of the component to elevated temperature can result in a change in the shape of the component.

It will often be appropriate for the method to include a forming step after the heat treatment of step (b) but before the heating step (c) of the method, especially by cold working the component. One or more such forming steps can enable high levels of deformations to be imparted to an article without breaking the component. The heat treatment step (b) can be repeated after the forming step. The method of the invention can include one, two, three or more such forming operations. There will generally be heat treatment steps (b) between the forming operations, and often also after the last of the forming operations and before the subsequent heating step (c) of the method.

The method of the invention can be performed on Ni—Ti based shape memory alloys. Such alloys include binary alloys, such as those in which the nickel content is at least about 50 at. %, preferably at least about 50.5 at. %. The nickel content will usefully be less than about 52 at. %, preferably less than about 51 at. %. The method can also be performed on other Ni—Ti based alloys, including alloys with ternary and quaternary additions. Examples of elements that can be incorporated in the alloy include Cr, Fe, Co, Al and Cu. Added elements can be present in amounts up to about 10 at. %, preferably up to about 5 at. %. Alloys which are suitable for this treatment are preferably thermally unstable, meaning that their properties can be altered through thermal ageing after quenching from above the solvus temperature. It is understood that certain alloying additions may cause the specific temperatures cited to change somewhat, and that appropriate corrections be made.

Preferably, the alloy for the component and the treatment of the component are selected so that the $A_f$ temperature of the alloy in the treated component is approximately 0° to 40° C. below the operating temperature of the component when in use.

The method of the invention can be used to produce components for use in a wide variety of applications. The components can be used in medical devices, for example tools and devices which are to be implanted in a human or animal body. An example of an implant device is a stent which can be positioned in a lumen in a body while in a transversely compressed configuration and then made to expand transversely into contact with the wall of the lumen, to support the lumen or to force the wall outwardly. This transverse expansion can result from discharge of the stent from a tubular constraint, for example in a catheter. The expansion can involve the release of energy stored in the component by virtue of the enhanced elastic properties of a shape memory alloy.

DESCRIPTION OF THE PREFERRED EMBODIMENTS

Figure 1:
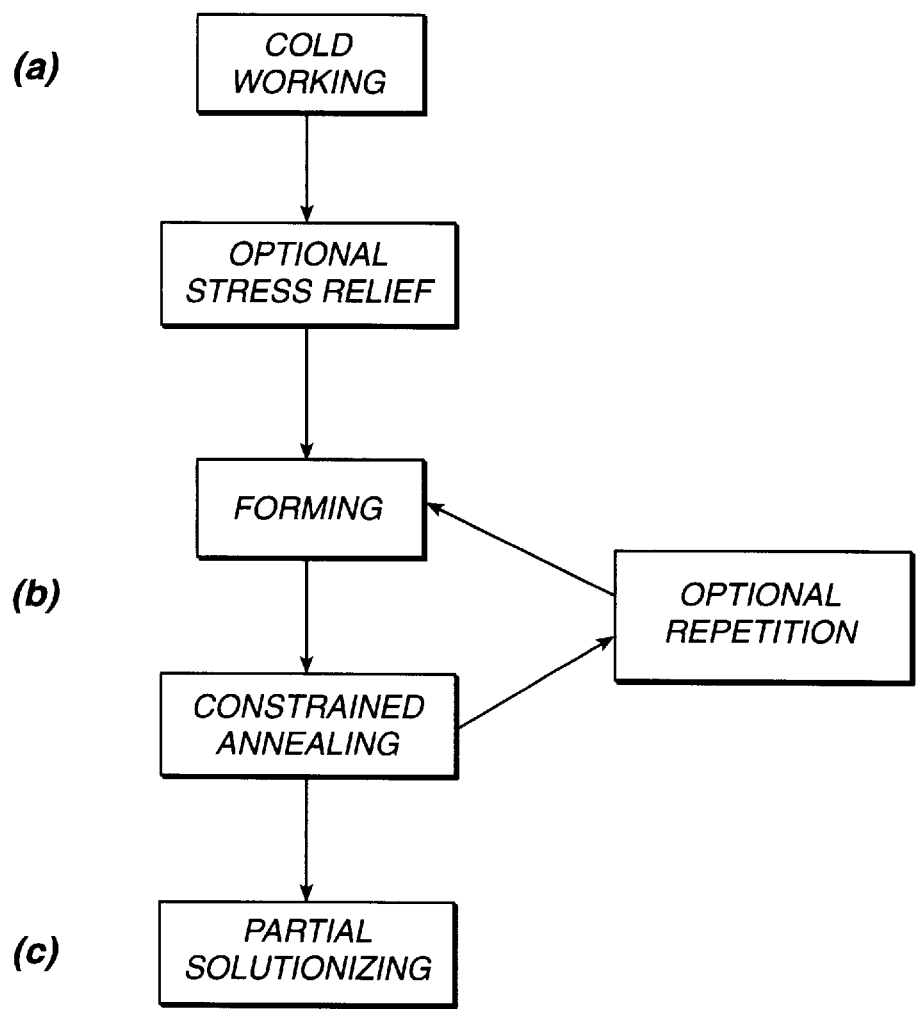
FIG. 1 is a block diagram providing schematic representation of the steps of the method of the invention.

A component formed from a Ni—Ti based shape memory alloy, which is to be treated by the method of the invention so that the component exhibits superelasticity, is produced by appropriate step(s) involving for example, machining, working, heat treatment steps and so on. After a prior annealing step, the component is subjected to one or more cold working steps, for example by drawing, swaging, pressing, mandrel expansion etc. A stress relief heat step can be included after the after cold working step in order to reduce the amount of retained cold work or to improve ductility. If such an optional heat treatment is performed, it is necessary to avoid removing too much cold work. This stress relief heating step is conducted without constraint.

The component is then formed into a desired shape, and subjected to a heat treatment while it is restrained in the desired configuration. This operation can be repeated several times in order to achieve a final desired component configuration. Alternatively, the forming and shape setting heat treatment might be combined into one hot forming operation. In this case, the temperature and time of the hot forming operation will be those discussed above for the shape setting heat treatment.

When the desired configuration is achieved, it is subjected to an additional heating step at elevated temperature higher than that of the final shape setting treatment, but lower than the solvus temperature of the alloy, for a short period to cause the $A_f$ temperature of the component to be reduced. This final treatment can be performed with or without constraining the component in a desired shape.

The method of the invention can be used to make a stent for delivery to a blood vessel in a human or animal body in a catheter. Such a stent might be formed from a tube of a Ni—Ti binary alloy containing from 50.5 to 52 at. % nickel. The solvus temperature of such an alloy is about 580° C. The tube will have an external diameter of about 1.5 mm and a wall thickness of about 0.25 mm. The characteristic transformation temperature $A_f$ of the tube (before shape setting) will be approximately 10° C. A pattern can be cut into the tube, for example by means of a laser (as is known). The pattern will be selected so that the resulting part has a desired flexibility an ability to exert force against the wall of the blood vessel or other lumen.

The tube can be expanded from its configuration as cut so that its external dimension increases to 4 mm. This can be done be successively passing mandrels of diameters 2 mm, 3 mm and 4 mm through the device, and heat treating the device on each of these mandrels at about 450° C. for about 10 minutes. The characteristic transformation temperature $A_f$ of the alloy after the all steps are performed is about 35° C. (producing a device that is no longer superelastic at room temperature).

The component is then subjected to a final heat treatment after the end of the shape setting steps, at a temperature between 510° and 530° C. for about 1 minute. The characteristic transformation temperature $A_f$ of the alloy after the heat treatment step is about 25° C., making the device substantially superelastic at room temperature, and ideally superelastic at body temperature.

The component can be deformed inwardly from the final configuration resulting from the heat treatment step towards the configuration prior to cold work, and the deformation substantially recovered elastically relying on the superelastic properties imparted to the alloy by the method of the invention.

What is claimed is:

1. A method of treating a component formed from a Ni—Ti based shape memory alloy so that the component exhibits superelasticity and to impart a desired shape to the component and thereafter lower the component's Af, which comprises:

(a) cold working the component, the component comprising greater than 50.5 at. % nickel;

(b) restraining the alloy to a desired shape and heat treating the alloy at a temperature that is less than solvus temperature of the alloy, to cause dislocations in the alloy resulting from the cold working step to combine; and (c) after heat treating the component in the restrained desired shape in step (b), removing the restraint and thereafter heat treating the component at a temperature that is greater than the temperature to which it is exposed in step (b) and less than the solvus temperature of the alloy, causing the component to retain the desired shape and causing the Af temperature to be reduced so that said component is superelastic at body temperature.

2. A method as claimed in claim 1, further including the step of annealing the component prior to step (a) and wherein the amount of cold work imparted to the component in step (a) is greater than about 10%.

3. A method as claimed in claim 1, in which the component is exposed to elevated temperature in step (c) for not more than about 10 minutes.

4. A method as claimed in claim 3, in which the component is exposed to elevated temperature in step (c) for not more than about 5 minutes.

5. A method as claimed in claim 1, in which the component is exposed to elevated temperature in step (c) for at least about 30 seconds.

6. A method as claimed in claim 1, in which step (b) is carried out more than once but before step (c) is carried out.

7. A method as claimed in claim 1, in which the alloy is a thermally unstable alloy.

8. A method as claimed in claim 1, in which the heat treatment of step (c) is performed at a temperature above 510° C.

* * * * *